United States Patent [19]

Uno et al.

[11] 4,237,135

[45] Dec. 2, 1980

[54] 2-(4-ETHYL-1-PIPERAZINYL)-4-PHENYL-QUINOLINE, PROCESS FOR PREPARATION THEREOF, AND COMPOSITION THEREOF

[75] Inventors: Hitoshi Uno, Takatsuki; Yasutaka Nagai, Muko; Tadahiko Karasawa, Toyonaka; Kiyoshi Furukawa, Ibaraki, all of Japan

[73] Assignee: Dainippon Pharmaceutical Co., Ltd., Osaka, Japan

[21] Appl. No.: 22,779

[22] Filed: Mar. 22, 1979

[30] Foreign Application Priority Data

Mar. 29, 1978 [JP] Japan ................................. 53-37029

[51] Int. Cl.³ .................. A61K 31/495; C07D 401/04
[52] U.S. Cl. ...................................... 424/250; 544/363

[58] Field of Search .......................... 544/363; 424/250

[56] References Cited

U.S. PATENT DOCUMENTS

| 3,576,809 | 4/1971 | Stauffer | 544/363 |
|-----------|--------|----------|---------|
| 3,668,207 | 6/1972 | Carney | 544/363 |
| 3,737,540 | 6/1973 | Rodriguez | 544/363 |

Primary Examiner—Paul M. Coughlan, Jr.
Attorney, Agent, or Firm—Stevens, Davis, Miller & Mosher

[57] ABSTRACT 2-(4-Ethyl-1-piperazinyl)-4-phenylquinoline and its pharmaceutically acceptable acid addition salts, which are useful as antidepressant agents in the treatment of depression or depressive state in mammals including humans, and processes for the preparation thereof.

9 Claims, No Drawings

2-(4-ETHYL-1-PIPERAZINYL)-4-PHENYLQUINOLINE, PROCESS FOR PREPARATION THEREOF, AND COMPOSITION THEREOF

The present invention relates to a new compound, 2-(4-ethyl-1-piperazinyl)-4-phenylquinoline and its pharmaceutically acceptable acid addition salts which are useful as antidepressants, and processes for the preparation thereof, method for using the same and also a pharmaceutical composition containing the compounds as the essential active ingredient.

2-(4-Ethyl-1-piperazinyl)-4-phenylquinoline of the present invention has the following formula:

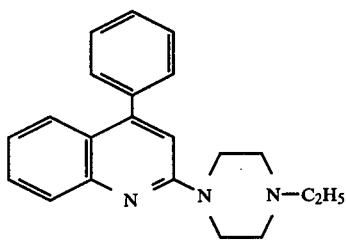

[I]

The pharmaceutically acceptable acid addition salt of the above compound [I] includes salt with inorganic acids such as hydrochloric acid, hydrobromic acid, hydriodic acid, sulfuric acid, phosphoric acid, etc., and organic acids such as citric acid, maleic acid, fumaric acid, tartaric acid, benzoic acid, lactic acid, methanesulfonic acid, etc. These salts may be in the form of a hydrate, and hence, the compounds of the present invention include such hydrates.

Some analogous compounds are disclosed in U.S. Pat. Nos. 3,542,785 and 3,668,207. These U.S. patents disclose the compounds of the formula:

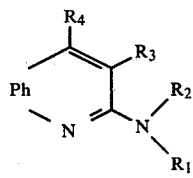

[II]

wherein Ph is a 1,2-phenylene radical, $R_1$ is hydrogen, amino or an aliphatic hydrocarbon radical, $R_2$ is an aliphatic or araliphatic hydrocarbon radical, $R_3$ is hydrogen, an aliphatic, araliphatic or aromatic radical and $R_4$ is a carbocyclic or heterocyclic, mono- or bi-cyclic aromatic radical. These broad definitions may theoretically include the compound [I] of the present invention, but the specifically disclosed compounds which are analogous to the compound [I] are only those of the formula:

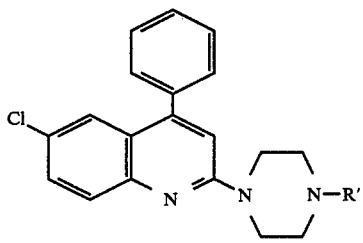

[III]

wherein R' is methyl or phenyl radical, i.e. 6-chloro-2-(4-methyl-1-piperazinyl)-4-phenyliquinoline and 6-chloro-2-(4-phenyl-1-piperazinyl)-4-phenylquinoline. Moreover, the U.S. patents disclose that these compounds of the formulae [II] and [III] have an anti-inflammatory or diuretic activity, which are essentially different from the antidepressant activity of the compound [I] of the present invention. As is disclosed hereinafter, it has experimentally been confirmed that the compound [I] of the present invention and its salts have more valuable pharmacological properties that the known analogous compounds of the formula [III].

Furthermore, there is disclosed in Helv. Chim. Acta, Vol. 60, pages 1644–1649 (1977) a further analogous compound of the formula:

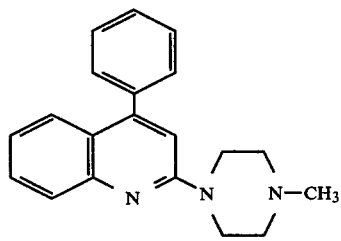

[IV]

but this literature does not disclose any pharmacological activity of this compound [IV].

As a result of the present inventors' extensive studies on agents acting on the central nervous system, it has been found that these compounds of the formulae [I] and [IV] and also some higher homologues such as 2-(4-n-propyl-1-piperazinyl)-4-phenylquinoline and 2-(4-n-butyl-1-piperazinyl)-4-phenylquinoline and their pharmaceutically acceptable salts have excellent pharmacological properties and further that the compound [I] of the present invention is particularly superior in an antidepressant activity which is seen with the currently available antidepressants such as imipramine.

The compound of the formula [I] and its pharmaceutically acceptable salts show in experimental animals the pharmacological properties suggestive of antidepressant potential, such as anti-reserpine activity (reversal of hypothermia and catalepsy), anti-tetrabenazine activity (reversal of ptosis), suppression of mouse-killing behavior of olfactory bulb-ablated rats, inhibition of brain noradrenaline turnover, etc., and therefore, are useful as an antidepressant agent.

The pharmacological characteristics of the compound [I] and its pharmaceutically acceptable salts are as follows:

(1) Their antidepressangt activity is more potent than that of imipramine.

(2) They possess the properties to inhibit spontaneous and methamphetamine-induced locomotor activities and also to enhance brain dopamine turnover, like neuroleptics, all of which are not seen with the currently available tricyclic antidepressants.

(3) They also possess an anti-tremorine activity (anti-tremor effect) which is characteristic of the currently available antiparkinsonian agents, and their potency is much more potent than that of imipramine.

The compound [I] can be prepared by the processes as disclosed in U.S. Pat. Nos. 3,542,785 and 3,668,207 and Helv. Chim. Acta. Vol. 60, pages 1644–1649 (1977). For instance, the compound [I] can be prepared by reacting a compound of the formula:

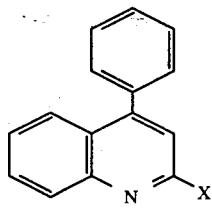
[V]

wherein X is a leaving atom or group, with 1-ethylpiperazine.

The leaving atom or group X in the formula [V] denotes any atom or group which can leave off in the form of HX under the reaction conditions together with hydrogen atom bonded to the nitrogen atom at 4-position of 1-ethylpiperazine. Examples of the leaving atom or group include halogen atoms such as chlorine or bromine, lower alkylthio groups, preferably those having 1 to 4 carbon atoms, such as methylthio, ethylthio, propylthio or butylthio, arylsulfonyloxy groups such as benzenesulfonyloxy or p-toluenesulfonyloxy, and alkylsulfonyloxy groups such as methanesulfonyloxy.

The reaction of the compound [V] with 1-ethylpiperazine is usually carried out in a solvent, such as aromatic hydrocarbons (e.g. toluene, xylene, etc.), lower alkanones (e.g. methyl ethyl ketone, etc.), ethers (e.g. dioxane, diglyme, etc.), dimethylformamide, dimethyl sulfoxide, or the like. This reaction is preferably carried out in the presence of a base, but instead of using a base, an excess amount of 1-ethylpiperazine may be used. The base includes alkali metal carbonates (e.g. sodium carbonate, potassium carbonate, etc.), alkali metal bicarbonates (e.g. sodium bicarbonate, potassium bicarbonate, etc.), and tertiary amines (e.g. triethylamine, etc.). Reaction temperature is preferably in the range of 100° to 140° C. The starting compound [V] can be prepared by the process as disclosed in J. Am. Chem. Soc., Vol. 70, pages 2402–2404 (1948) and U.S. Pat. No. 3,668,207.

Alternatively, the compound [I] can be prepared by ethylating 4-phenyl-2-(1-piperazinyl)quinoline. The ethylation can be carried out by a conventional process, for example, by treating 4-phenyl-2-(1-piperazinyl)quinoline with an ethylating agent of the formula:

C₂H₅—Y [VI]

wherein Y is a residue of a reactive ester of an alcohol. The residue of a reactive ester of an alcohol includes, for example, halogens (e.g. chlorine, bromine or iodine), arylsulfonyloxy groups (e.g. benzenesulfonyloxy, p-toluenesulfonyloxy), alkylsulfonyloxy groups (e.g. methanesulfonyloxy), ethoxysulfonyloxy group, or the like. Suitable examples of the ethylating agent are ethyl iodide, diethyl sulfate, ethyl p-toluenesulfonate, or the like.

The reaction of 4-phenyl-2-(1-piperazinyl)quinoline with the ethylating agent [VI] is usually carried out in a solvent, such as aromatic hydrocarbons (e.g. benzene, toluene, xylene, etc.), lower alkanones (e.g. methyl ethyl ketone, etc.), ethers (e.g. dioxane, etc.), dimethylformamide, or the like. This reaction is also preferably carried out in the presence of the base as mentioned hereinbefore. Reaction temperature is preferably in the range of 70° to 160° C. The starting 4-phenyl-2-(1-piperazinyl)quinoline can be prepared, for example, by reacting the compound [V] with piperazine.

The desired compound prepared by the above processes can be isolated from the reaction mixture and purified in a usual manner.

The compound [I] can be obtained in the form of a free base or a salt thereof owing to the kinds of the starting material and reaction conditions. When the compound is obtained in the form of a salt thereof, it is easily converted into the free base by treating it with a base such as an alkali metal hydroxide in a usual manner, and on the other hand, when it is obtained in the form of a free base, it is easily converted into the acid addition salt thereof by treating it with a pharmaceutically acceptable acid as mentioned hereinbefore in a usual manner.

Pharmacological experiments have been done on the compound of the present invention, some known and novel analogous compounds and an antidepressant on the market, as mentioned below. In the experiments, ED₅₀ was calculated by Litchfield-Wilcoxon method.

(Compound of the present invention)

A: 2-(4-Ethyl-1-piperazinyl)-4-phenylquinoline dihydrochloride (Reference Compounds)

1: 6-Chloro-2-(4-methyl-1-piperazinyl)-4-phenylquinoline dihydrochloride which is disclosed in U.S. Pat. Nos. 3,542,785 and 3,668,207.

2: 6Chloro-2-(4-phenyl-1-piperazinyl)-4-phenylquinoline which is disclosed in U.S. Pat. Nos. 3,542,785 and 3,668,207.

3: 2-(4-Methyl-1-piperazinyl)-4-phenylquinoline which is disclosed in Helv. Chim. Acta, 60, 1644–1649 (1977).

4: 2-(4-n-Propyl-1-piperazinyl)-4-phenylquinoline dihydrochloride which is novel and prepared in a similar manner as described in Examples of the present specification, m.p. 225°–230° C.

5: 2-(4-n-Butyl-1-piperazinyl)-4-phenylquinoline dimaleate which is novel and prepared in a similar manner as described in Examples of the present specification, m.p. 167°–168° C.

6: Imipramine which is a currently available antidepressant and whose chemical name is 5-(3-dimethylaminopropyl)-10,11-dihydro-5H-dibenz[b,f]azepine.

TEST 1: ANTIDEPRESSANT ACTIVITY (1) Anti-reserpine activity (a) Antagonistic effect on hypothermia induced by reserpine This effect was examined according to the method of B. M. Askew [Life Sci. 2, 725 (1963)], using male STD-ddY strain mice weighing 20–25 g. Each test compound was given orally to the mice (each group: 5 animals) in 6 different doses, and immediately 5mg/kg of reserpine was injected intraperitoneally. Rectal temperature of each mouse was measured 4 hours later with a thermister (Shibaura Electric, BMG III-130). The effective dose 50 ($ED_{50}$) was calculated for each compound. The $ED_{50}$ means the dose of test compound in which the reserpine-induced fall of rectal temperature was inhibited by 50%.

(b) Antagonistic effect on catalepsy induced by reserpine

Male STD-ddY strain mice, weighing 20–15 g, were used in groups of 10 mice each. Groups of mice received an intraperitoneal injection of 5 mg/kg of reserpine, and 5 hours later each test compound was given thereto orally in 7 different doses. The mice were tested for catalepsy 1 hour after the administration of test compounds. $ED_{50}$ was calculated for each compound. The $ED_{50}$ means the dose of test compound in which the mice were protected from the reserpine-induced catalepsy by 50% in number.

(2) Anti-tetrabenazine activity (Antagonistic effect on ptosis induced by tetrabenazine)

Male STD-ddY strain mice, weighing 20–25 g, were used in groups of 10 mice each. Each test compound was given orally to the mice in 7 different doses, and 1 hour later 70 mg/kg of tetrabenazine was injected intraperitoneally. Two hours after the tetrabenazine injection, the degree of eyelid closure (ptosis) was assessed on the basis of macroscopic scoring (0: no closure of the eyelid, 1: 1/4 closure, 2: 2/4 closure, 3: 3/4 closure and 4: complete closure), essentially according to the method of P. A. J. Janssen [Arzneim. Forsch. 15, 104 (1965)]. $ED_{50}$ was calcuated for each compound. The $ED_{50}$ means the dose of test compound in which the tetrabenazine-induced ptosis was inhibited by 50% in degree.

The results of the experiments (1) and (2) are shown in Tables 1 and 2, wherein the test compounds have the following formula:

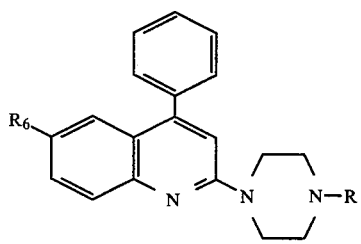

TABLE 1

| Anti-reserpine activity | | | | |
|---|---|---|---|---|
| Test compound | | | $ED_{50}$ (mg/kg, p.o.) | |
| No. | $R_6$ | R | Hypothermia | Catalepsy |
| A | H | $C_2H_5$ | 5.8 | 1.5 |
| 1 | Cl | $CH_3$ | 30.8 | 20.0 |
| 2 | Cl | $C_6H_5$ | >100 | >100 |
| 6 | Imipramine | | 21.5 | 38.3 |

TABLE 2

| Anti-reserpine and anti-tetrabenazine activities | | | | |
|---|---|---|---|---|
| | | | $ED_{50}$ (mg/kg, p.o.) | |
| Test compound | | Anti-reserpine | | Anti-tetrabenazine |
| No. | $R_6$ | R | Hypothermia | Catalepsy | (Ptosis) |
| A | H | $C_2H_5$ | 5.8 | 1.5 | 1.8 |
| 3 | H | $CH_3$ | 13.9 | 4.7 | 10.4 |
| 4 | H | n-$C_3H_7$ | 13.6 | 4.4 | 8.2 |
| 5 | H | n-$C_4H_9$ | 13.7 | 6.3 | 29.9 |
| 6 | Imipramine | | 21.5 | 38.3 | 4.9 |

It is evident from Table 1 that compound A of the present invention possesses a more potent anti-reserpine activity than imipramine does. That is, the potencies of compound A in antagonizing the hypothermia and catalepsy induced by reserpinde are 3.7 and 25.5 times more powerful than those of imipramine, respectively.

In contrast, an analogous compound, compound 2 is devoid of the anit-reserpine activity. Moreover, compound 1 which is structurally analogous to compound A is 5 and 13 times less active than compound A in antagonizing the hypothermia and catalepsy induced by reserpine, respectively.

Furthermore, it is evident from Table 2 that compound A of this invention is 2.4 to 5.8 times more powerful than its lower homologue, compound 3 in both anti-reserpine and anti-tetrabenazine potencies. In addition, compound A is 2–17 times more potent than compounds 4 and 5, which are higher homologues of compound A.

(3) Suppressing effect on mouse-killing behavior in olfactory bulb-ablated rats

Male Wistar strain rats, weighing 240–260 g, which had developed mouse-killing behavior after ablation of the olfactory bulb according to the method of Z. P. Horovitz [Int. J. Neuropharmacol. 5, 405 (1966)], were used in groups of 15 animals each. Each test compound was given intraperitoneally to the rats in 6 different doses, and 1 hours later the rats were each tested as to whether they killed a mouse or not. $ED_{50}$ was calculated for each compound. The $ED_{50}$ means the dose in which a compound inhibited the mouse-killing behavior in half of the rats. The results are shown in Table 3.

TABLE 3

| Suppressing effect on mouse-killing behavior of olfactory bulb-ablated rats | |
|---|---|
| Test compound | $ED_{50}$ (mg/kg, i.p.) |
| A | 5.0 |
| 6 | 5.5 |

As shown in Table 3, compound A of this invention is as potent as imipramine in suppressing the mouse-killing behavior of olfactory bulb-ablated rats.

TEST 2: NEUROLEPTICS-LIKE ACTIVITY (1) Inhibitory effect on spontaneous locomotor activity Male mice of STD-ddY strain, weighing 20–25 g, were used in groups of 5 mice each. Each test compound was given orally to the mice in 5 different doses, and 2 hours later the spontaneous locomotor activity of each mouse was measured for 3 minutes by means of an Animex locomotor activity meter (made by Farad Electronics). $ED_{50}$ was calculated for each compound. The $ED_{50}$ means the dose of test compound in which the locomotor activity was reduced to 50% of that of control group receiving saline.

(2) Anti-methamphetamine effect (Inhibitory effect on methamphetamine-induced locomotor activity)

Male STD-ddY strain mice, weighing 20-25 g, were used in groups of 10 mice each. Groups of mice were injected intraperitoneally with 4 mg/kg of methamphetamine, and 30 minutes later each test compound was injected intraperitoneally in 3 different doses. One hour after the injection of methamphetamine, locomotor activity of each mouse was measured for 10 minutes with an Animex locomotor activity meter.

The results of the experiments (1) and (2) are shown in Table 4.

TABLE 4

Inhibitory effect on spontaneous and methamphetamine-induced locomotor activities

| Test compound | ED$_{50}$ (mg/kg) Spontan. (p.o.) locomotor | Anti-methamphetamine (i.p.) |
|---|---|---|
| A | 58.7 | 8.0 |
| 1 | >200 | >30 |
| 2 | >200 | >30 |
| 3 | 56.4 | 12.9 |
| 4 | 62.2 | 13.2 |
| 5 | 50.6 | 16.4 |
| 6 | >200 | >30 |
| 7* | 7.4 | 1.00 |

*Chlorpromazine which is a currently available neuroleptic and whose chemical name is 2-chloro-10-(3-dimethylaminopropyl)phenothiazine.

It is evident from Table 4 that compound A of the present invention is about ⅛ as active as chlorpromazine in inhibition of spontaneous and methamphetamine-induced locomotor activities.

Compound 3, the lower homologue of compound A, and compounds 4 and 5, the higher homologues of compound A, are as potent as compound A in inhibition of spontaneous locomotion, but somewhat less potent than that in antagonizing methamphetamine-induced locomotor activity.

In contrast, compounds 1 and 2, which are analogues of compound A, and imipramine are devoid of both activities.

Thus, it is suggested from the results of Tests 1 and 2 that compound A of the present invention is more potent than its analogues, compounds 1 and 2 and also than imipramine in the antidepressant activity. In addition, compound A shows some neuroleptics-like effects such as inhibition of spontaneous and methamphetamine-induced locomotor activities, which are not seen with compounds 1 and 2 nor with imipramine.

Though compound 3 is comparable to compound A in the potency of neuroleptics-like activity, the former compound is much less potent than the latter in the antidepressant activity.

Furthermore, the higher homologues of compound A, compounds 4 and 5 also are inferior to compound A in antidepressant potency.

TEST 3: EFFECT ON BRAIN MONOAMINE METABOLITES

Male Wistar strain rats, weighing 160-180 g, were used in groups of 5 rats each. Each test compound was given orally to the rats in a dose of 100 mg/kg and, 1, 3 and 6 hours later the rats were sacrificed. The brain concentrations of homovanillic acid (HVA), 3-methoxy-4-hydroxyphenylethylene glycol sulfate (MOPEG-SO$_4$), and 5-hydroxyindoleacetic acid (5-HIAA) were determined according to the method of Karasawa [Life Sci. 15, 1465 (1974)] for HVA and 5-HIAA and to the method of J. L. Meek [Br. J. Pharmacol. 45, 435 (1972)] for MOPEG-SO$_4$. The concentrations of the monoamine metabolites were calculated in terms of ng/g wet brain tissue and expressed as % of the concentrations of controls receiving saline. The results are shown in Table 5.

TABLE 5

Effect on brain monoamine metabolites

| Test Compound | Time (hour) | % of control HVA | MOPEG-SO$_4$ | 5-HIAA |
|---|---|---|---|---|
| A | 1 | 193* | 82* | 118 |
|   | 3 | 186* | 70* | 110 |
|   | 6 | 186* | 63* | 116 |
| 6 | 1 | 110 | 87* | 88 |
|   | 3 | 98 | 80* | 84* |
|   | 6 | 103 | 70* | 73* |

*P<0.01

As is evident from Table 5, compound A of the present invention causes a marked increase in brain HVA concentration, suggesting an enhanced turnover of brain dopamine by this compound. In contrast, imipramine is devoid of such activity.

Moreover, compound A, like imipramine, causes a significant decrease in brain MOPEG-SO$_4$ concentration, suggesting that compound A reduces the turnover of brain noradrenaline, just as imipramine does.

However, compound A does not affect brain 5-HIAA concentration. This fact suggests that compound A shows no effect on serotonin turnover in the brain. In this respect, compound A is distinct from imipramine.

TEST 4: ANTIPARKINSONIAN DRUG-LIKE ACTIVITY; ANTI-TREMORINE ACTIVITY (ANTAGONISTIC EFFECT ON TREMORINE-INDUCED TREMOR)

Male STD-ddY strain mice, weighing 20-25 g, were used in groups of 5 mice each. Each test compound was given orally to the mice in 5 different doses, and 2 hours later 20 mg/kg of tremorine was injected intraperitoneally. Half an hour after the injection of tremorine, each mouse was examined macroscopically for tremor severity, according to the rating scale with the scores 0, 1, 2, and 3 depending on the severity. ED$_{50}$ was calculated for each compound. The ED$_{50}$ means the dose of test compound in which the tremorine-induced tremor was inhibited by 50% in severity.

TABLE 6

Anti-tremorine activity

| Test compound | ED$_{50}$ (mg/kg, p.o.) |
|---|---|
| A | 9.7 |
| 6 | 48.3 |
| 8* | 11.4 |

*Biperiden which is a currently available anti-parkinsonian drug and whose chemical name is α-5-norbornen-2-yl-α-phenyl-1-piperidinepropanol.

As shown in Table 6, compound A of the present invention is more potent than imipramine and almost comparable to biperiden in the anti-tremorine activity.

TEST 5: ACUTE TOXICITY

Male STD-ddY strain mice, weighing 20-25 g, were used. Each test compound was given orally or intraperitoneally to the mice (each group: 10 mice) in 5 to 7 different doses, and their mortality was examined during the observation period of 7 days. The median lethal dose ($LD_{50}$) was calculated for each compound by the probit method.

Toxicity of compound A is comparable to or somewhat weaker than that of imipramine, as indicated in Table 7.

TABLE 7

| | Acute toxicity | |
|---|---|---|
| | $LD_{50}$ (mg/kg) | |
| Test compound | p.o. | i.p. |
| A | 568 | 119 |
| 6 | 400 | 100 |

As is clear from the above experimental results, the compound of the formula [I] and its pharmaceutically acceptable salts have potent antidepressant activity and also some neuroleptics- and antiparkinsonian drug-like activities with low toxicity. According, the compounds of the present invention are useful as an antidepressant for the treatment of depression or depressive state in mammals including humans. Their pharmacological profile suggests that they are particularly effective in the treatment of depression or depressive state with anxiety or agitation or both and also in the treatment of parkinsonism with depressive symptoms.

The compounds of the present invention can be administered in oral, parenteral or rectal route, but preferably in oral route. The dose of these compounds varies with the administration routes, the age of the patients, the kinds and severity of the diseases to be treated, or the like, but are in the range of 0.1 to 6 mg, preferably 0.2 to 4 mg, as the free base per kg of body weight per day for humans. The dose may be divided and administered in two to four times per day The compound [I] and its pharmaceutically acceptable salts are usually used in the form of a pharmaceutical composition which contains them in an effective and nontoxic amount in admixture with conventional pharmaceutical carrier materials suitable for oral, parenteral or rectal application and being unreactive with the active compound [I] and its salts. Suitable examples of the carrier materials are lactose, starch, sucrose, microcrystalline cellulose, sodium carboxymethylcellulose, calcium carboxymethylcellulose, methylcellulose, gelatin, acacia, hydroxypropylcellulose, hydroxypropyl methylcellulose, polyvinylpyrrolidone, light anhydrous silicic acid, magnesium stearate, talc, titanium dioxide, sorbitan fatty acid ester, glycerides of saturated fatty acid, macrogol, propylene glycol, benzyl alcohol, water, or the like. The pharmaceutical composition may be in the dosage form of tablets, capsules, granules, fine granules, powders, syrups, suppositories, injections, or the like. These preparations may be prepared by conventional methods. Liquid preparation may be prepared by dissolving or suspending the active compounds in water or other suitable vehicles, when used. Tablets may be coated in a conventional manner. For injection, the preparation may be prepared by dissolving a pharmaceutically acceptable acid addition salt of the compound [I] in distilled water for injection, if necessary, followed by making isotonic with isotonic agents such as glucose, saline or the like, and further, other ingredients such as pH adjusting agents and preservatives may be admixed thereto. These pharmaceutical compositions contain usually as the active ingredient the compound [I] or its pharmaceutically acceptable salt in the ratio of 0.5% by weight or more, preferably 1 to 60% by weight, based upon the whole weight of the compositions. The compositions may also contain one or more other therapeutically active compounds.

The present invention is illustrated by the following Examples but is not limited thereto. In the Examples, the compound was identified with the elemental analysis, mass spectrum, IR spectrum, NMR spectrum, etc.

EXAMPLE 1

2-(4-Ethyl-1-piperazinyl)-4-phenylquinoline

A solution of 2.0 g of 2-chloro-4-phenylquinoline and 2.7 g of 1-ethylpiperazine in 15 ml of toluene was heated under reflux for 10 hours. To the reaction mixture was added water and the resulting mixture was extracted with ethyl acetate. The extracts were dried over anhydrous sodium sulfate and concentrated under reduced pressure. The residue was chromatographed on silica gel (25 g) using chloroform as an eluent. Fractions containing the title compound were pooled and concentrated to give the title compound (2.3 g, 87% ), m.p. 87°–88° C.

The free base thus obtained was treated with ethanolic hydrogen chloride to give the dihydrochloride of the title compound. Recrystallization from ethanol gave the pure dihydrochloride, m.p. 225°–230° C.

EXAMPLE 2

4-phenyl-2-(1-piperazinyl)quinoline

Repeating the procedure of Example 1 using anhydrous piperazine in place of 1-ethylpiperazine gave the title compound, m.p. 133°–134° C.

EXAMPLE 3

2-(4-Ethyl-1-piperazinyl)-4-phenylquinoline

A stirred suspension of 3.0 g of 4-phenyl-2-(1-piperazinyl)quinoline, 1.9 g of ethyl iodide and 1.1 g of sodium carbonate in 30 ml of methyl ethyl ketone was heated under reflux for 12 hours. The reaction mixture was concentrated under reduced pressure. To the residue was added water and the resulting mixture was extracted with ethyl acetate. The dried extracts were concentrated to give an oily residue, which was chromatographed on silica gel (30 g) using chloroform as an eluent. There was obtained the title compound (2.8 g, 85%), m.p. 87°–88° C.

EXAMPLE 4

| | per 1,000 tablets |
|---|---|
| 2-(4-Ethyl-1-piperazinyl)-4-phenylquinoline dihydrochloride | 5 g |
| Corn starch | 33 g |
| Lactose | 75 g |
| Microcrystalline cellulose | 30 g |
| Hydroxypropylcellulose | 5 g |
| Light anhydrous silicic acid | 1 g |
| Magnesium stearate | 1 g |

The above components were blended, granulated and made into 1,000 tablets each weighing 150 mg by a conventional method. The tablets were further coated with hydroxypropyl methylcellulose, talc, titanium dioxide, and sorbitan fatty acid ester in a customary manner. There were obtained 1,000 film coated tablets.

EXAMPLE 5

| | per 1,000 capsules |
|---|---|
| 2-(4-Ethyl-1-piperazinyl)-4-phenylquinoline dihydrochloride | 10 g |
| Corn starch | 49 g |
| Lactose | 15 g |
| Microcrystalline cellulose | 25 g |
| Talc | 0.5 g |
| Magnesium stearate | 0.5 g |

The above components were blended, granulated and filled into 1,000 capsules by a conventional method.

EXAMPLE 6

| | per 1,000 tablets |
|---|---|
| 2-(4-Ethyl-1-piperazinyl)-4-phenylquinoline dihydrochloride | 25 g |
| Corn starch | 34 g |
| Lactose | 80 g |
| Microcrystalline cellulose | 53 g |
| Polyvinylpyrrolidone | 6 g |
| Light anhydrous silicic acid | 1 g |
| Magnesium stearate | 1 g |

The above components were blended, granulated and made into 1,000 tablets each weighing 200 mg by a conventional method. The tablets were further coated in a similar manner as described in Example 4.

What is claimed is:

1. 2-(4-Ethyl-1-piperazinyl)-4-phenylquinoline.

2. A pharmaceutically acceptable acid addition salt of 2-(4-ethyl-1-piperazinyl)-4-phenylquinoline.

3. 2-(4-Ethyl-1-piperazinyl)-4-phenylquinoline dihydrochloride.

4. A pharmaceutical composition comprising an antidepressant effective amount of 2-(4-ethyl-1-piperazinyl)-4-phenylquinoline or a pharmaceutically acceptable acid addition salt thereof, and a pharmaceutically acceptable carrier.

5. The pharmaceutical composition of claim 4 wherein the active ingredient is 2-(4-ethyl-1-piperazinyl)-4-phenylquinoline dihydrochloride.

6. A method of treating depression or depressive state in humans which comprises administering to a patient an effective amount of 2-(4-ethyl-1-piperazinyl)-4-phenylquinoline or a pharmaceutically acceptable acid addition salt thereof.

7. The method of claim 6 wherein said compound is 2-(4-ethyl-1-piperazinyl)-4-phenylquinoline dihydrochloride.

8. The method of claim 6 or 7 wherein said compound is administered in a daily dosage of from 0.1 to 6 mg/kg of body weight as the free base.

9. The method of claim 8, wherein said daily dosage is in the range of 0.2 to 4 mg/kg of body weight as the free base.

* * * * *